(12) United States Patent
Rogachefsky

(10) Patent No.: US 9,421,049 B2
(45) Date of Patent: Aug. 23, 2016

(54) INTRAMEDULLARY ROD FIXATION SYSTEM

(71) Applicant: Richard A. Rogachefsky, San Pedro, CA (US)

(72) Inventor: Richard A. Rogachefsky, San Pedro, CA (US)

( * ) Notice: Subject to any disclaimer, the term of this patent is extended or adjusted under 35 U.S.C. 154(b) by 249 days.

(21) Appl. No.: 14/020,484

(22) Filed: Sep. 6, 2013

(65) Prior Publication Data

US 2015/0073414 A1 Mar. 12, 2015

(51) Int. Cl.
*A61B 17/72* (2006.01)
*A61B 17/17* (2006.01)
(Continued)

(52) U.S. Cl.
CPC ....... *A61B 17/7291* (2013.01); *A61B 17/1725* (2013.01); *A61B 17/725* (2013.01); *A61B 17/7208* (2013.01); *A61B 17/164* (2013.01);
(Continued)

(58) Field of Classification Search
CPC ................ A61B 17/7291; A61B 17/1725; A61B 17/7208; A61B 17/725; A61B 17/8645; A61B 17/164; A61B 17/863; A61B 17/564
USPC ......... 606/62, 64, 65, 66, 67, 301, 305, 308, 606/309, 88, 89, 98, 316, 317, 321, 102, 606/104
See application file for complete search history.

(56) References Cited

U.S. PATENT DOCUMENTS 4,913,137 A * 4/1990 Azer et al. ...................... 606/64
5,066,296 A 11/1991 Chapman et al.
(Continued)

FOREIGN PATENT DOCUMENTS

DE 4343117 A1 6/1995

OTHER PUBLICATIONS

Orbay et al.: The Treatment of Unstable Metacarpal and Phalangeal Shaft Fractures with Flexible Nonlocking and Locking Intramedullary Nails; Hand Clin 22, pp. 279-286 (Elsevier Saunders 2006).
(Continued)

*Primary Examiner* — Pedro Philogene
*Assistant Examiner* — David C Comstock
(74) *Attorney, Agent, or Firm* — Andrew J. Anderson, Esq.; Harter Secrest & Emery LLP

(57) ABSTRACT

A method for fixation of a fracture of a bone having an intramedullary canal. An intramedullary rod is inserted into the intramedullary canal of the bone, wherein the intramedullary rod includes at least one proximal hole and at least one distal hole. Proximal and distal screws or pegs are inserted through the bone and through the proximal and distal holes in the rod, wherein the proximal and the distal screws or pegs are headless screws or pegs and are selected to have a size and are inserted through the proximal and distal holes in the rod such that the screws or pegs do not extend substantially beyond an exterior surface of the bone. Further described are apparatus and a kit for intramedullary fixation of fractures of bones of the hand. The methods, apparatus and kits of the invention are advantageously designed for percutaneous placement of intramedullary rods into the intramedullary canal of metacarpal or phalanx bones of the hand to stabilize fractures, and in particular in the proximal or middle phalanx bones of the hand. Rotational control is provided by locking screws or pegs through the rod, also placed percutaneously. Specific alignment jigs, drills, screw drivers and equipment may be used for placement of the rod and screws, wherein the rod and screws will stabilize the fracture.

14 Claims, 7 Drawing Sheets

(51) Int. Cl.
  *A61B 17/86* (2006.01)
  *A61B 17/16* (2006.01)
  *A61B 17/56* (2006.01)

(52) U.S. Cl.
  CPC .......... *A61B 17/863* (2013.01); *A61B 17/8645* (2013.01); *A61B 2017/564* (2013.01)

(56) References Cited

U.S. PATENT DOCUMENTS

| | | | | |
|---|---|---|---|---|
| 5,281,224 A * | 1/1994 | Faccioli et al. | ......... | 606/62 |
| 6,322,562 B1 | 11/2001 | Wolter | | |
| 6,533,788 B1 | 3/2003 | Orbay | | |
| 6,932,818 B2 * | 8/2005 | Behrens | ......... | 606/64 |
| 8,157,803 B1 | 4/2012 | Zirkle, Jr. et al. | | |
| 2003/0073999 A1 | 4/2003 | Putnam | | |
| 2003/0083661 A1 | 5/2003 | Orbay et al. | | |
| 2008/0294163 A1 | 11/2008 | Chou et al. | | |

OTHER PUBLICATIONS

Orbay: Intramedullary Nailing of Metacarpal Shaft Fractures; Techniques in Hand and Upper Extremity Surgery, vol. 9, Issue 2, pp. 69-73 (Lippincott Williams & Wilkins 2005).
Gonzalez et al.: Intramedullary Fixation of Metacarpal and Proximal Phalangeal Fractures of the Hand; Clinical Orthopaedics and Related Research, No. 327, pp. 47-54 (Lippincott-Raven 1996).
Stryker: VariAx Distal Radius Locking Plate System, Operative Technique, Liturature No. 90-07799 (Stryker 2008).
International Search Report and Written Opinion of the International Searching Authority in corresponding International Application No. PCT/US2014/054332, mailed Dec. 30, 2014 (8 pages).

* cited by examiner

INTRAMEDULLARY ROD FIXATION SYSTEM

FIELD OF THE INVENTION

This invention relates generally to intramedullary rod fixation systems. More specifically, this invention relates to an intramedullary rod fixation system employing intramedullary rods and locking screws or pegs especially useful for surgical treatment of fractures of bones of the hand.

BACKGROUND OF THE INVENTION

The hand is one of the most intricate and complex structures of the human body. It is a complex structure made of bone and soft tissue. The structures work in a precise and extremely well coordinated way to produce well coordinated and precise movements. The hand can perform a wide variety of function and is capable of both strength and power or fine motor and sensory function. Any disruption to the anatomic structures can cause profound loss of function and disability to not only the hand, but the patient as a whole. The hand performs range of motion, strength and fine motor skills such as pinch.

The bones of the hand provide the scaffold that support all other structures of the hand. The hand bones include the metacarpals, proximal phalanges, middle phalanges and distal phalanges. The joints of the hand are the carpometacarpal, metacarpophalangeal, proximal interphalangeal, and distal interphalangeal joints. Each joint is stabilized by ligaments. Motion to the hand is provided by the gliding of a complex array of tendons. Each finger has two flexor tendons that bend the fingers and one or two extensor tendons that straighten the fingers. These tendons are in close proximity to the bone especially at the phalangeal level. The flexor tendons are held close to the bone by a sheath or tunnel. The extensor tendons extend over the phalanges and form a complex extensor mechanism to straighten the fingers.

The coordinated action of the flexor and extensor tendons provide flexion and extension for the fingers and full range of motion of the hand. When the extensor muscles in the forearm contract, they pull on the extensor tendons of the hand, and straighten the fingers. When the flexor muscles in the forearm contract, they pull the flexor tendons in the hand, which flex the fingers. In addition, intrinsic muscles in the hand contribute to hand motion and strength.

It is the coordinated effort of the muscles and tendons in the forearm and hand that provides hand function. If the skeletal system or the highly intricate soft tissue structures are disrupted the function of the hand is compromised.

Hand fractures are some of the most common fractures that occur. The mechanisms in which hand fractures occur are varied. The most common cause of hand fractures is due to trauma. Hand fractures can be in the form of simple fractures, resulting, e.g., from lower energy trauma such as ground level falls or punching mechanism, or complex fractures, resulting, e.g., from high energy mechanisms such as motor vehicle accidents or falls from a significant height. Other causes of hand fractures are pathologic from bone tumors.

Most fractures that occur in the hand are simple stable fractures that can be treated conservatively without surgery. Conservative treatment methods commonly used are casting or splints. Fractures treated with these methods heal the vast majority of the time with good results (Ref. 1, Ref. 2).

More severe fractures that occur, such as unstable fractures, comminuted fractures or open fractures of the hand, are more problematic to treat. Many times conservative cast or splint treatment does not provide enough stability to the fracture and the fracture heals in a mal-united or angled position. This causes loss of function of the hand.

For the more severe fractures surgical intervention is indicated. Presently, open reduction and internal fixation (ORIF) with plates and screws, or screws alone, are most commonly used (Ref. 3). The advantage of open reduction and internal fixation is that good anatomic alignment and stability can be obtained. The inherent anatomy of the hand and fingers demonstrates that the flexor and extensor tendons are in close proximity to the bone. They are separated from the bone surface by a thin soft tissue layer. It is paramount that to regain function of the hand, unimpeded gliding of the tendons occurs during fracture healing.

The disadvantage of open reduction and internal fixation is the disruption of the soft tissues and especially the extensor mechanism during surgical dissection. Once the soft tissue layer between the bone and tendon or tendon itself is disrupted, tendon adherence to the hardware or bone commonly occurs. This compromises tendon function and ultimately hand function.

This situation occurs most commonly when proximal and middle phalangeal fractures occur at the finger level. In this area the tendon structures are in very close proximity to the bone surface. Fractures and injury that occur in these regions either by trauma or surgery lead to a high incidence of tendon adherence and loss of finger motion. Many surgical exposures for open reduction and internal fixation of metacarpal, proximal and middle phalangeal fractures are through the dorsal aspects of the hand and fingers. Tendon adherence is less often an issue in the dorsal aspect of the hand for metacarpal fractures during open reduction and internal fixation surgery, due to the fact that the extensor tendons are not as close to the bone surface. There is a greater amount of soft tissue between the bone and the tendons. Also, extensor tendons over the metacarpal region of the hand have greater excursion and glide over a greater area.

The most problematic area for surgical intervention is for fractures of the proximal and middle phalangeal region. In these areas the extensor mechanism is only separated from the bone by a thin tissue layer. The placement of hardware on the dorsal aspect of the bone or radial or ulnar aspects, as most commonly done, leads to a high incidence of the extensor tendon adhering to the hardware due to the close proximity of the tendon. This leads to loss of tendon gliding and loss of motion of the finger. Most commonly extensor lag or drooping of the finger occurs. Later surgeries such as freeing up the tendon from scar and removal of the hardware have less than satisfactory results. Once the extensor mechanism is disrupted through trauma and scarring usually there is permanent damage.

Techniques to avoid the problem of tendon adherence include placement of percutaneous Kirschner wires (K wires) through the skin to hold the fracture in place. Percutaneous placement of screws alone to join bone fragments has also been advocated. These techniques can be technically demanding and require indirect reduction, and typically provide less stable fixation than obtained with plates and screws in many instances.

To decrease soft tissue trauma during surgery, intramedullary devices and rods have been developed for stabilization of other fractures such as the femur, tibia and humerus and have become a mainstay of treatment. They provide stable internal fixation with less trauma to the soft tissues (Ref. 4, Ref. 5, Ref. 6). Locking screws employed with such conventional intramedullary devices typically comprise headed screws, wherein in use the head of the screw extends beyond the exterior surface of the bone.

Intramedullary devices have been developed for hand fractures (Ref. 3, Ref. 7, Ref. 8, Ref. 9). Orbay U.S. Pat. No. 6,533,378 discloses an intramedullary rod system with a proximal locking device for treatment of simple fractures of the metacarpal and proximal phalanx. The rod provided good translational control, but does not control rotation adequately (Ref. 9).

Gonzalez et al. (Ref. 10, Ref. 11, Ref. 12) reported using intramedullary rods for both proximal phalanx and metacarpal fractures. The implants were indicated for transverse and short oblique fractures only. They also reported metacarpal rod system for comminuted fractures resulting from gunshot wounds that had locking capability, but open reduction and internal fixation was necessary to place the implant. Locking screws employed appear to be conventional screws with heads extending beyond the external surface of the bone.

Bio-absorbable rods have also been used for metacarpal and phalangeal fractures. The advantages of these implants are that they give stability to the fracture and are later absorbed, precluding hardware complications or removal. Disadvantages of these implants are that they have higher implant failure due to resorption of the implant, implant inflammatory reaction during resorption, and less rotational control (Ref. 13, Ref. 14).

References referred to above are:
Ref. 1: Stern P J. Fractures of the Metacarpals and Phalanges. In Green Operative Hand Surgery, 4th edition. 1999, pp 711-771;
Ref. 2: Tavassoli J, Ruland R T, Hogan C J, Cannon D L. Three Cast Techniques for the Treatment of Extra-articular Metacarpal Fractures. Comparison of short term Outcomes and Final Fracture Alignments. J Bone Joint Surg., Am (87-10) October 2005, pp. 2196-2201;
Ref. 3: Ozerk K, Gillani S, Williams A, Peterson S L, Morgan S. Comparison of Intramedullary Nailing versus Plate-Screw Fixation of Extra-articular Metacarpal fractures. J Hand Surg, Am. (33-10) December 2008, 1724-1731;
Ref. 4: Kreder H J, Schemitsch E H, Conlan L B, Wild L, McKee M D. Femoral Intramedullary Nailing: Comparison of Fracture Table and Manual Traction. A Prospective Randomized Study. J Bone Joint Surg. Am, 84-A, (9) pp. 1514-1521;
Ref. 5: Tornetta P, Tiburzi. Antegrade or Retrograde Reamed Femoral Nailing: A Prospective Randomized Trial. J Bone Joint Surg, Br., (82) 2000, pp. 652-654;
Ref. 6: Brumback R J. The Rational of Interlocking Nailing of the Femur, Tibia and Humerus. Clin Orthop Rel Res. (324) March 1996, pp. 292-320;
Ref. 7: Mockford B J, Thompson N S, Nolan P C, Calderwood J W. Antegrade Intramedullary Fixation of Displaced Metacarpal Fractures: A New Technique. Plastic Recon Surg. (111-1) January 2003, pp. 351-354;
Ref. 8: Downing N D, Davis T R. Intramedullary Fixation of Unstable Metacarpal Fractures. Hand Clinic, 22(3) August 2006, pp. 269-277;
Ref. 9: Depew Small Bone fixation System. Technique manual;
Ref. 10: Gonzalez M H, Igram C M, Hall R F. Intramedullary nailing of Proximal Phalanx Fractures. J Hand Surg (20-5) September 1995, pp 808-812;
Ref. 11: Gonzalez M H, Hall R F. Intramedullary Fixation of Metacarpal and Proximal Phalanx Fractures of the Hand. Clin Orth Rel Res. (327) June 1996, pp. 47-54;
Ref. 12: Busch H G, Gonzalez M H, Hall R F. Locked Intramedullary Nailing of Metacarpal Fractures Secondary to Gunshot wounds. J Hand Surg, Am (31-7) September 2006, pp. 1083-1087;
Ref. 13: Hughes T B. Bioabsorbable Implants in the Treatment of Hand Fractures: An Update. Clin Ortho Rel Res. (445) April 2006, pp. 169-174;
Ref. 14: Kumpta S M, Spinner R, Leung P C. Absorbable Intramedullary Implants for Hand Fractures. Animal Experiment and Clinical Trial. J Bone Joint Surg, Br., (74-4) July 1992, pp. 563-566.

SUMMARY OF THE INVENTION

In one aspect, the invention is directed towards a method for fixation of a fracture of a bone having an intramedullary canal comprising: inserting an intramedullary rod into the intramedullary canal of the bone, wherein the intramedullary rod includes at least one proximal hole and at least one distal hole; inserting a proximal screw or peg through the bone and through the at least one proximal hole; and inserting a distal screw or peg through the bone and through the at least one distal hole; wherein the proximal and the distal screws or pegs are headless screws or pegs and are selected to have a size and are inserted through the proximal and distal holes in the rod such that the screws or pegs do not extend substantially beyond an exterior surface of the bone. The intramedullary rod advantageously may be percutaneously inserted into the intramedullary canal of the bone, and the screws or pegs may be percutaneously inserting through the bone and through the holes in the rod. The invention is particularly useful for treating fractures for bones in the hand, wherein the bone is a metacarpal or phalangeal bone.

In another aspect, the invention is directed towards apparatus for intramedullary fixation of fractures of bones of the hand, comprising an intramedullary rod sized for insertion into a bone of the hand selected from metacarpal and phalanx bones, the intramedullary rod having at least one proximal hole and at least one distal hole; and headless screws or pegs having a diameter such that the screws or pegs are lockable in place by a friction fit with, or screw threads in, at least one of the proximal and distal holes of the intramedullary rod, and having lengths sized for the width of the selected bone of the hand such that the screws or pegs when locked in place with the rod do not extend substantially beyond an exterior surface of the selected bone of the hand when inserted through the proximal and distal holes in the rod.

In a further aspect, the invention is directed towards a kit for intramedullary fixation of fractures of bones of the hand, comprising a series of intramedullary rods with different size increments and lengths, sized for insertion into a plurality of different sized bones of the hand selected from metacarpal and phalanx bones, wherein the series includes at least one intramedullary rod having at least one proximal hole and at least one distal hole; and a series of headless screws or pegs having a diameter such that the screws or pegs are lockable in place by a friction fit with, or screw threads in, at least one of the proximal and distal holes of the intramedullary rod, and having lengths sized for various widths of the different sized bones of the hand so as to be selectable to enable use with the intramedullary rod having proximal and distal holes such that the screws or pegs when locked in place with the rod do not extend substantially beyond an exterior surface of a selected bone of the hand when inserted through the proximal and distal holes in the rod.

In preferred embodiments, the methods, apparatus and kits of the invention are advantageously designed for percutaneous placement of intramedullary rods into the proximal or middle phalanges intramedullary canal to stabilize fractures. Rotational control is provided by locking screws or pegs through the rod, also placed percutaneously. Specific alignment jigs, drills, screw drivers and equipment may be used for placement of the rod and screws, wherein the rod and screws will stabilize the fracture.

The invention is advantageous with regard to conventional use of plates and screws as the rod and screws will be placed with-in the bone so that tendon adherence does not occur. Also the rod and screws may be placed through small incisions percutaneously, minimizing trauma to the soft tissues, and tendons. Immediate stable internal fixation of the fracture may be obtained allowing immediate range of motion to the fingers and hand and accelerating return of motion and function. By decreasing the surgical trauma to the soft tissues and tendons and keeping the hardware within the bone and away from the extensor and flexor tendons tendon, adherence and injury may be avoided.

BRIEF DESCRIPTION OF THE SEVERAL VIEWS OF THE DRAWING(S)

DETAILED DESCRIPTION OF THE INVENTION

Figure 1A:
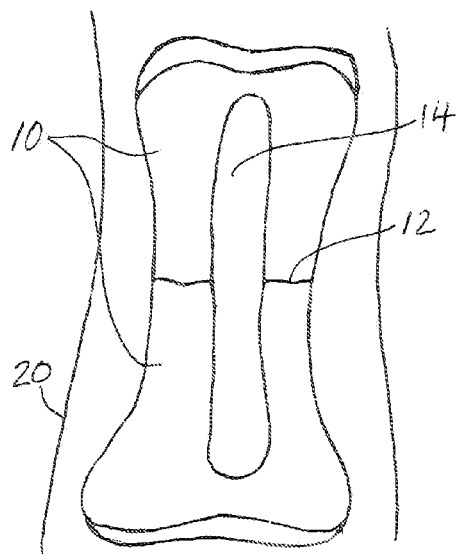
FIGS. 1A-1D and 2A-2H illustrate the percutaneous placement of an intramedullary rod and locking screws in accordance with a first embodiment of the invention.
Figure 1B:
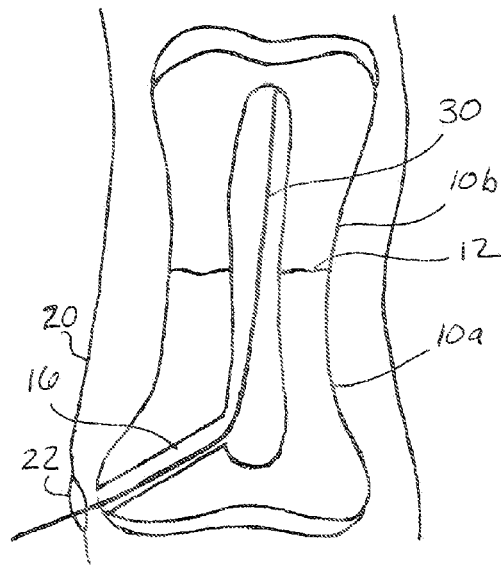
Figure 1C:
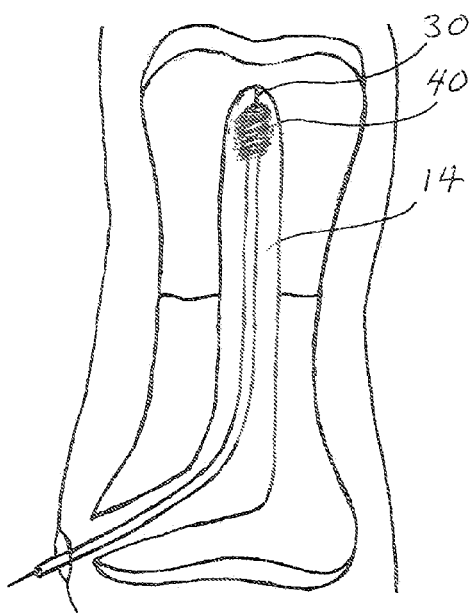
Figure 1D:
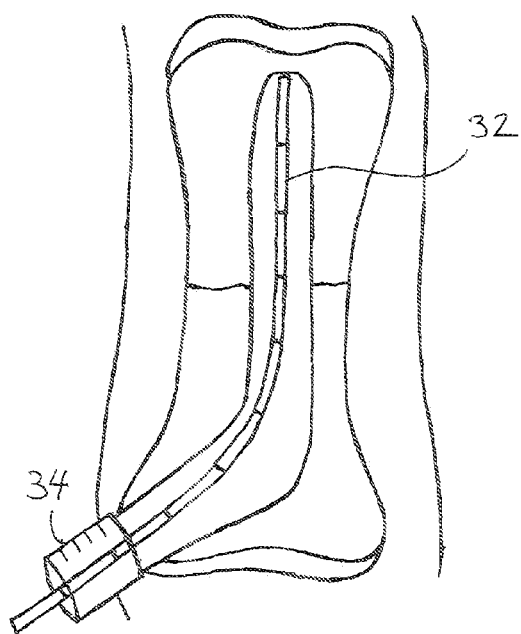

As shown in FIG. 1A, the technique for fixation of a fracture 12 in a bone 10 would be to first correct the fracture alignment by indirect reduction. Then a small incision 22 as shown in FIG. 1B would be made through the skin 20 and extensor tendon (not shown) down to the bone at the base of the bone. The base of the proximal phalanx would be used for fixation of a proximal phalanx fracture and the base of the middle phalanx would be used for fixation of a middle phalanx fracture. In one embodiment, an awl would be used to make an opening 16 in the base of the bone. The location of the awl and correct entrance into the bone would be verified under fluoroscopic x ray. Alternatively, the opening 16 in the base of the bone could be made with a drill and soft tissue guide. Then, as shown in FIG. 1B, a guide wire 30 would be placed through the opening 16, into the intramedullary canal 14 of the proximal fragment 10a, across the fracture 12 and into the intramedullary canal of the distal fragment 10b, further reducing the fracture. As shown in FIG. 1C, one or a series of small reamers 40 would then be placed over the guide wire and into the medullary canal of the bone. The opening 16 and canal 14 would be opened with the reamer, or a series of increasing diameter reamers, until the intramedullary canal was opened to an appropriate size to accommodate a desired intramedullary rod. The opening of the canal would be slightly larger than the rod for ease of passage of the rod through the curve from opening 16 to the canal 14. As shown in FIG. 1D, the reamer would be removed, and the length of the canal would be measured with a ruler. In one embodiment, a graduated sleeve 34 may be employed with a known length of guide wire. Alternatively, a calibrated guide wire 32 may be employed. In a further embodiment, a radiolucent ruler (not shown) which is visible upon x-ray may be employed.

Figure 2A:
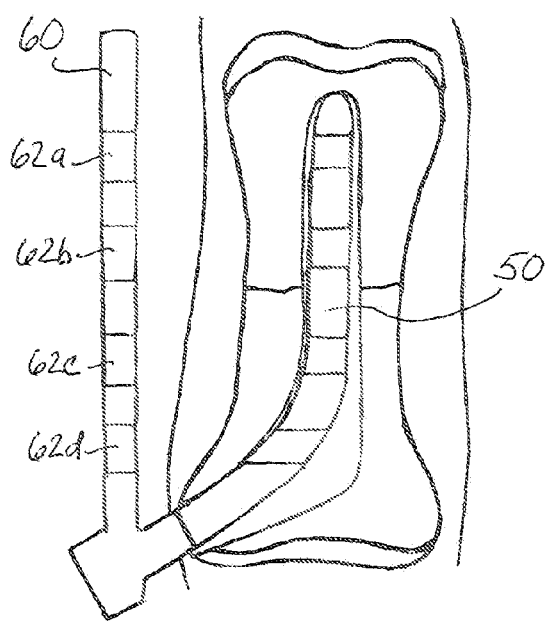
Figure 4:
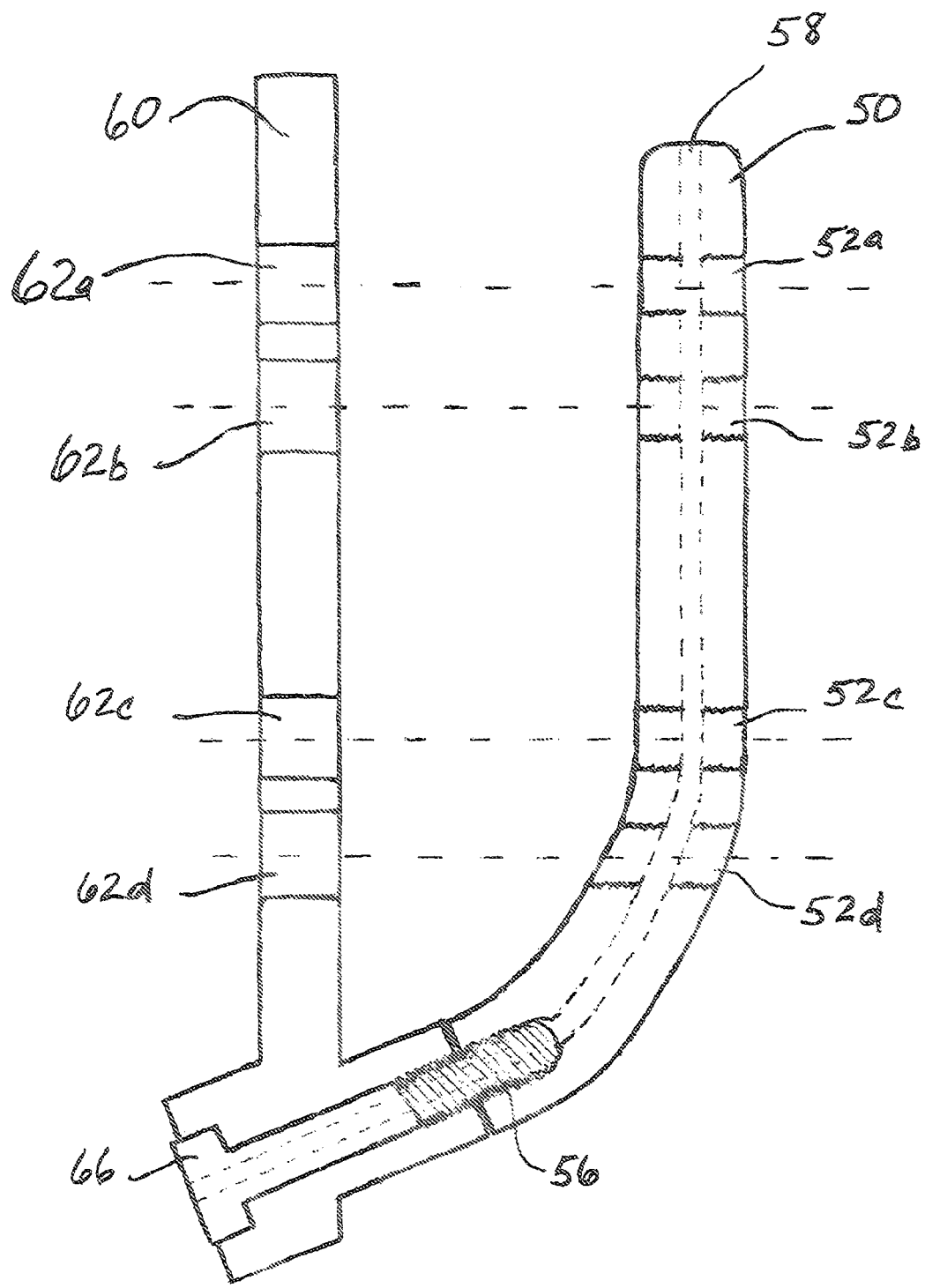
FIG. 4 illustrates releasable attachment of an alignment jig to an intramedullary rod.

As shown in FIG. 2A, an intramedullary rod 50 with an appropriate length and width would be placed into the intramedullary canal percutaneously with an alignment jig 60 releasably attached to the rod 50. As illustrated in FIG. 4, the alignment jig 60 may be attached to the rod 50, e.g., by an axial positioned bolt 66 extending through an end portion of the alignment jig, aligned with an end portion of the rod 50, where the bolt 66 engages threads 56 in an axial opening in the aligned end of the rod 50. Placement of the rod could be accomplished by pushing the rod attached on the jig into the canal by hand. Another technique to introduce the rod would be to have a striking platform on the jig and gently hammer the rod into the canal. The rod would be placed into the intramedullary canal of the proximal fragment, across the fracture and into the intramedullary canal of the distal fragment until the desired position was obtained and burying the rod in the bone. Fluoroscopy x ray would be used to determine correct alignment of the fracture and placement of the rod. The rod 50 and jig 60 (and axial bolt 66 releasably attaching the jig to the rod as shown in FIG. 4) may have an axial passageway 58 allowing for passage of the guide wire 30 there through. Alternatively, the guide wire may be removed prior to placement of the rod into the canal.

Figure 2B:
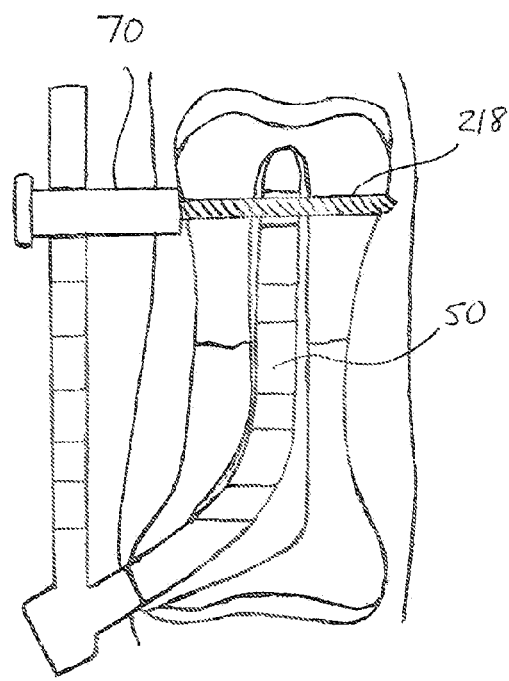
Figure 2C:
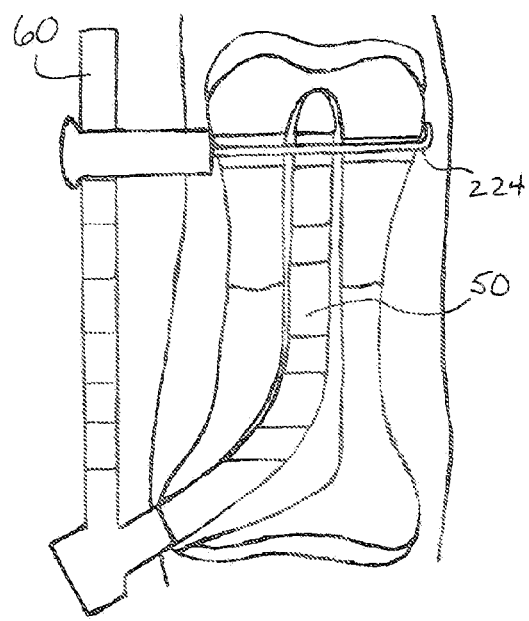
Figure 2D:
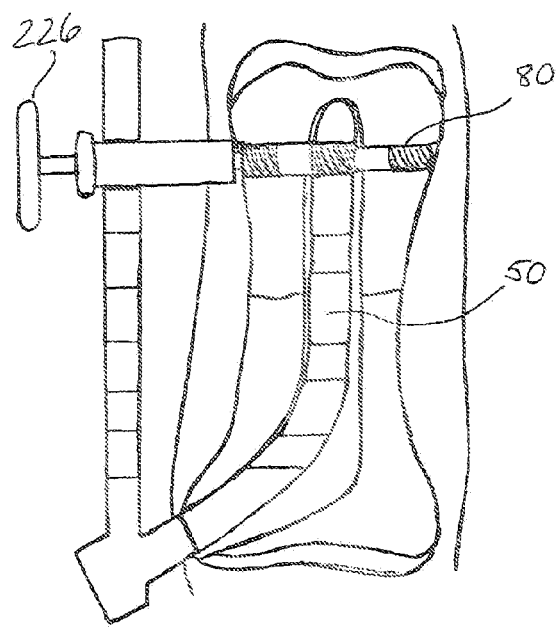

As shown in FIGS. 2B-2H, two to four screws or pegs would then be placed percutaneously through holes 52a-52d (FIG. 4) in the rod buried in the bone and locking the bone fracture fragments in place. The alignment jig 60 would be releasably attached to an end of the rod 50. As also further shown in FIG. 4, the alignment jig has guide holes 62a-62d aligned with the holes 52a-52d in the rod. A small incision would be placed through the skin and tendon down to the bone surface. As shown in FIG. 2B, a soft tissue sleeve 70 would be placed through a guide hole in the alignment jig down to the bone surface. The soft tissue sleeve would protect the soft tissue and tendon during drilling and insertion of the screw or peg. As further shown in FIG. 2B, a drill bit 218 attached to a drill (not shown) would be placed through the soft tissue sleeve drilling across the medial and lateral cortex of the bone. As shown in FIG. 2C, a depth gauge measuring device 224 would be used to measure the appropriate length screws or pegs. In accordance with one embodiment, as illustrated in FIG. 2D, a headless screw 80 with the desired length would be placed into the drilled hole through the medial cortex of the bone, across the corresponding hole in the rod and through the lateral cortex. The screw would be driven with screwdriver 226, and placed so that it did not extend substantially beyond the exterior surface of the bone, and preferably was flush with the medial and lateral cortex of the bone. Protuberance of the screw from the bone either at the tip or at the head of the screw can cause tendon adherence or snapping of the tendon over the prominent portion of the screw, thereby causing pain and limiting motion. Accordingly, the screw 80 is headless and is preferably placed flush with the bone cortex. This would avoid protuberance of the tip of the screw and the head. Screws would be locked into place by engagement with screw threads in a hole 52a-52d in the intramedullary rod.

Figure 2E:
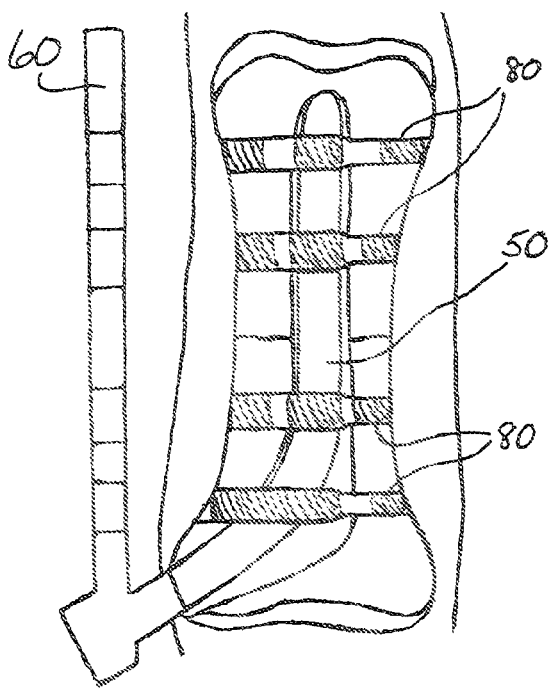

As further shown in FIG. 2D, screw 80 may be further locked in place by threads of the screw engaging the bone cortex. In one such embodiment, the threads of the screw engaging the bone and screw threads in the hole of the intramedullary rod are preferably of the same screw thread pitch, so as to avoid compressive stress on the bone, as such compressive stress may lead to new fractures, or propagation of the existing fracture. As shown in FIG. 2E, the process is repeated for insertion of additional screws 80 in the remaining proximal and distal holes of the rod 50.

Figure 5:
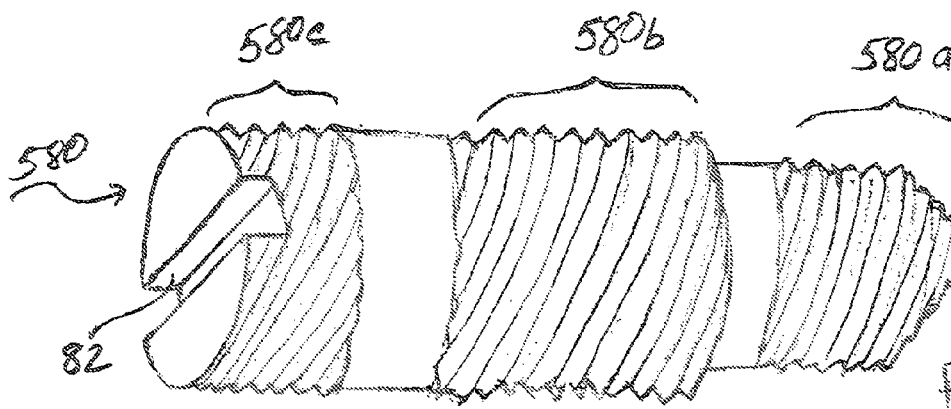
FIGS. 5 and 6 illustrate tapered screws which may be employed in various embodiments of the invention.
Figure 6:
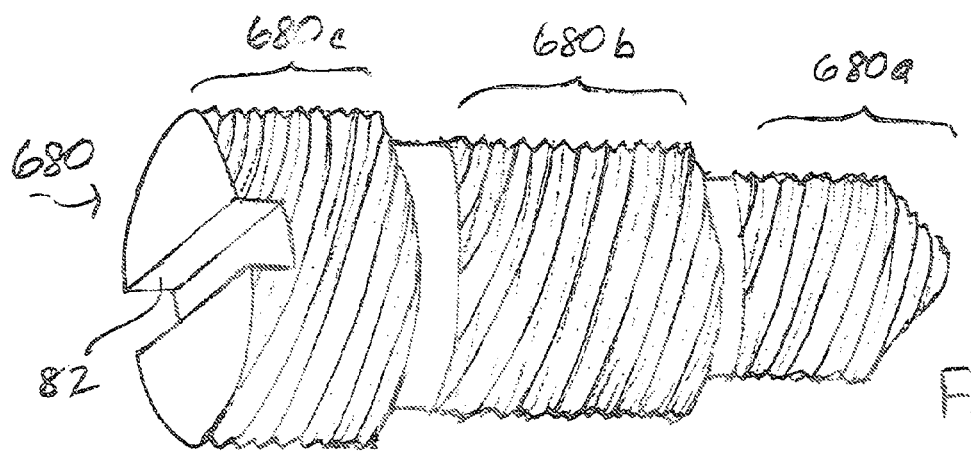

In a specific embodiment, screws 80 may have a tapered diameter, such that the screw diameter is narrower at the far cortex end than the diameter of the screw where the screw engages the screw threads in the hole of the intramedullary rod. When using such tapered diameter screws, a series of drill bits with corresponding different diameters may be employed to drill pilot holes of different diameters in the near and far cortex aligned with a hole in the rod, such that a relatively narrower diameter drill bit is used to extend through the hole in the rod and drill a screw pilot hole in the far cortex of the bone, so as not to damage the screw threads in the hole in the rod. In such tapered screw embodiment, the screw diameter at the near cortex end where the screw engages the bone may be equal to or greater than the diameter of the screw where the screw engages the screw threads in the hole of the intramedullary rod. Tapered screws which may be employed in various embodiments of the invention are illustrated in FIGS. 5 and 6. In FIG. 5, screw 580 includes a narrower end 580a and a relatively wider central portion 580b, sized to engage screw threads in a hole in a rod 50, and headless end portion 580c. In FIG. 6, screw 680 includes a relatively narrower end 680a, a central portion 680b sized to engage screw threads in a hole in a rod 50, and a relatively wider headless end portion 680c. As shown in FIGS. 5 and 6, though headless, screws 580 and 680 (as well as 80) preferably include a slot 82 or other opening for engagement with a driving device, such as a screwdriver or allen wrench. As shown in FIG. 4, guide holes 62a-62d in alignment jig 60 may be of greater diameter than holes 52a-52d in rod 50. This would accommodate a soft tissue sleeve 70 of greater diameter so as to guide drilling of an aligned wider diameter hole in the near cortex of the bone. Smaller diameter sleeves may be nested inside such a wider diameter sleeve, so as to accommodate aligned drilling of a narrower hole in the far cortex of the bone.

Figure 2F:
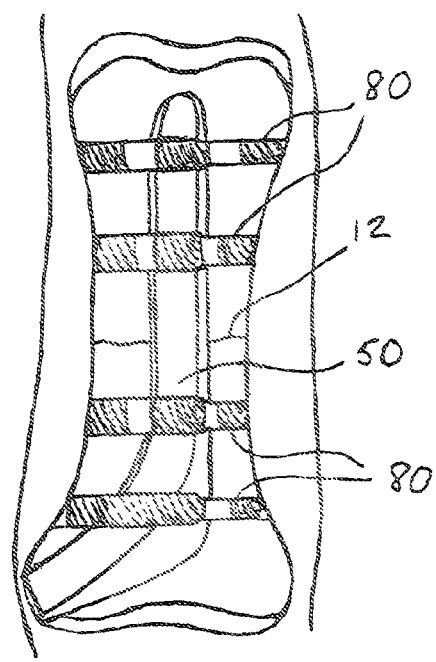

Once the crossing screws are locked in place, the alignment jig would be removed from the rod 50 as shown in FIG. 2F (e.g., with a screw driver to remove bolt 66 releasably attaching jig 60 to rod 50 as shown in FIG. 4). The final correct alignment of the fracture 12, rod 50 and screws 80 would be verified grossly by visual inspection of the finger and under fluoroscopic x ray. The small incisions would be closed with suture.

Figure 2G:
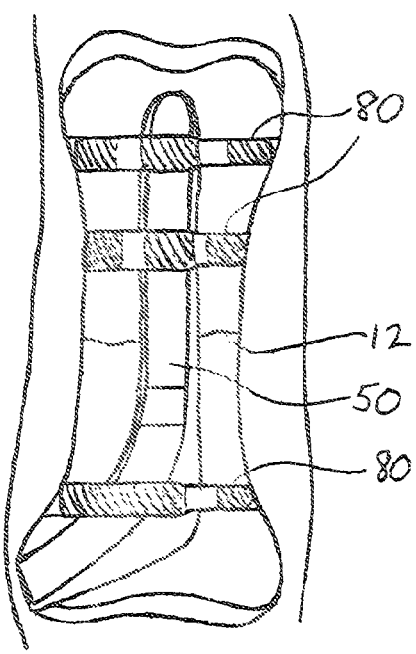
Figure 2H:
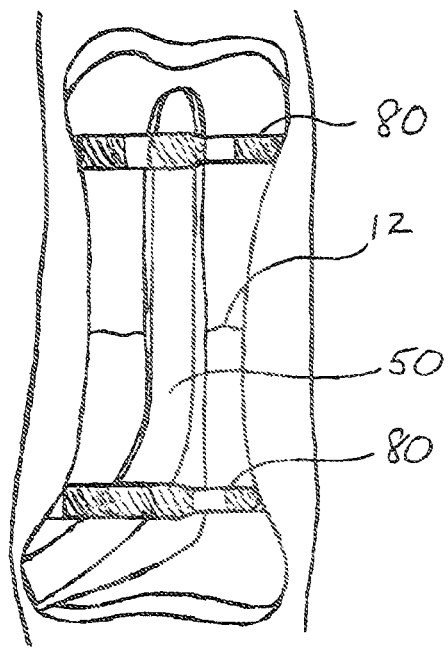

In alternative embodiments, less than four screws may be employed to lock the bone fragments into place. Selected holes in rod 50 may be left unused, e.g., as shown in FIG. 2G, or rods may be employed with any specific desired number of holes for a desired number of screws. A single screw may be inserted at each of the proximal and distal ends of rod a 50, e.g., as shown in FIG. 2H. In further embodiments, one or more additional screws may be inserted at either end of rod 50 as may be desired. Alignment jig 60 may include more than four guide holes and rod 50 may include more than four corresponding aligned holes therein to allow for selected spacing of cross screws 80. The holes in rod 50 and the guide holes in the alignment jig 60 may further be aligned at various angles to provide angled placement of screws through the bone fragments if desired.

Figure 7:
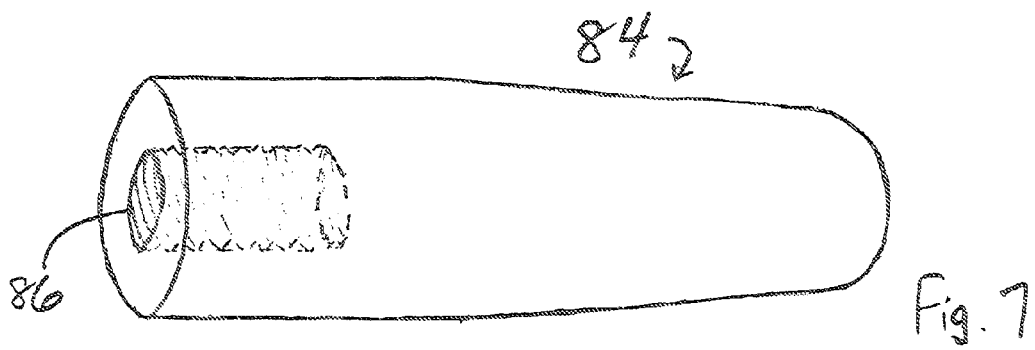
FIG. 7 illustrates a peg having a threadless external surface which may be employed in various embodiments of the invention.

In further alternative embodiments of the invention, pegs may instead be placed through holes 52a-52d in the rod 50 and bone to lock the rod in place by a friction fit between the external surface of the pegs with the rod, or with the rod and the bone cortex. In such an embodiment, as shown in FIG. 7, pegs 84 which have a threadless external surface may be employed, where the pegs have a gradually tapered diameter, so as to frictionally engage a hole in a rod at a selected depth corresponding to the position of the peg having a diameter equal to the diameter of the hole. Peg 84 may also include a threaded axial opening 86 for engaging a threaded end of a removal device (not shown). Pegs may also have a stepped tapered diameter, similarly as screws 580 and 680.

In the various embodiments of the invention, screws 80, 580, 680 and pegs 84 may be coated or otherwise surface treated, in particular at the exposed end surface thereof, with a silicone or a polytetrafluoroethylene polymer or copolymer material, or other bone growth inhibiting material, so as to inhibit bone growth thereon, to facilitate later removal of the screws and pegs if desired.

In another embodiment, the rod 50 may be a rod placed into the intramedullary canal percutaneously without the use of guide wires or reaming. They would have holes proximally and distally for placement of the locking screws or pegs as illustrated in the figures as described above, but the rod could be employed without placement of locking screws or pegs if enough stability is obtained from the rod only. This would be determined by the operating surgeon. Post operatively, immediate occupational therapy and range of motion would be started. Fracture healing would be assessed by serial x rays.

Figure 3A:
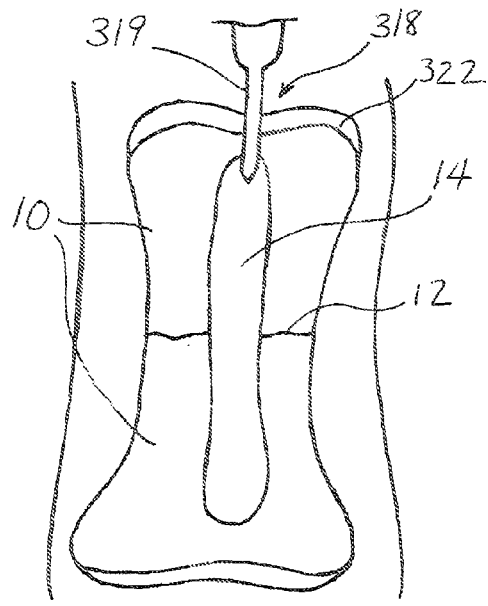
FIGS. 3A-3H illustrate the percutaneous placement of an intramedullary rod and locking screws in accordance with a second embodiment of the invention.
Figure 3B:
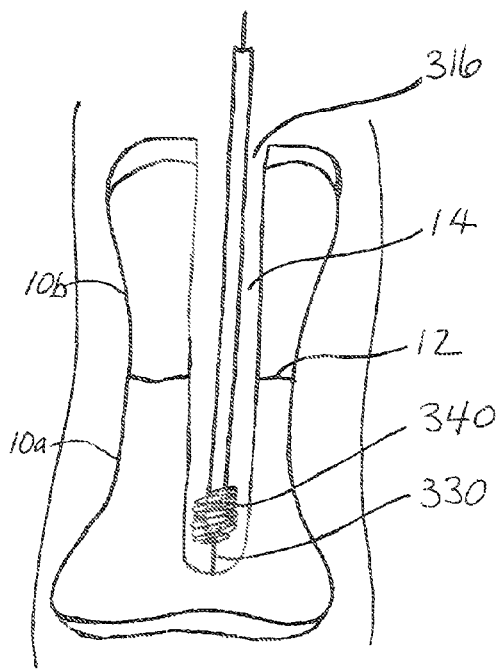
Figure 3C:
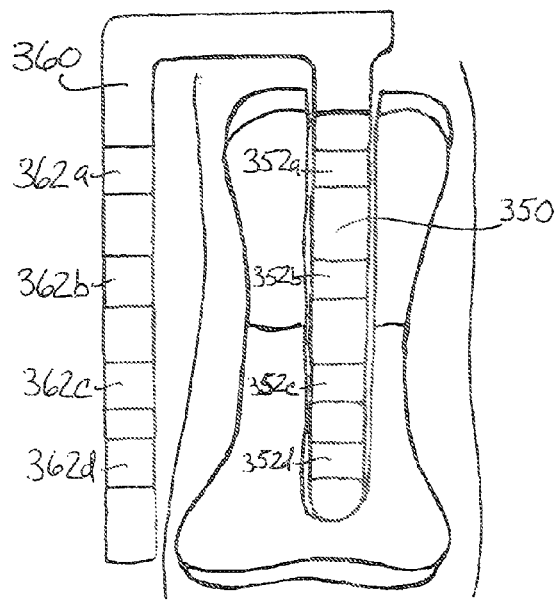
Figure 3D:
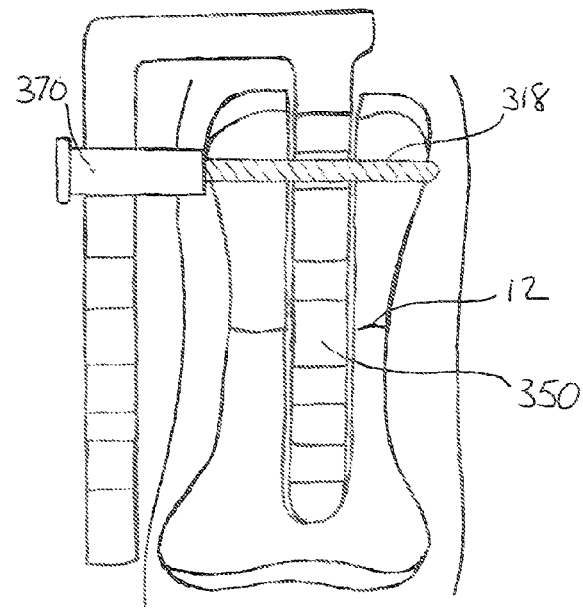
Figure 3E:
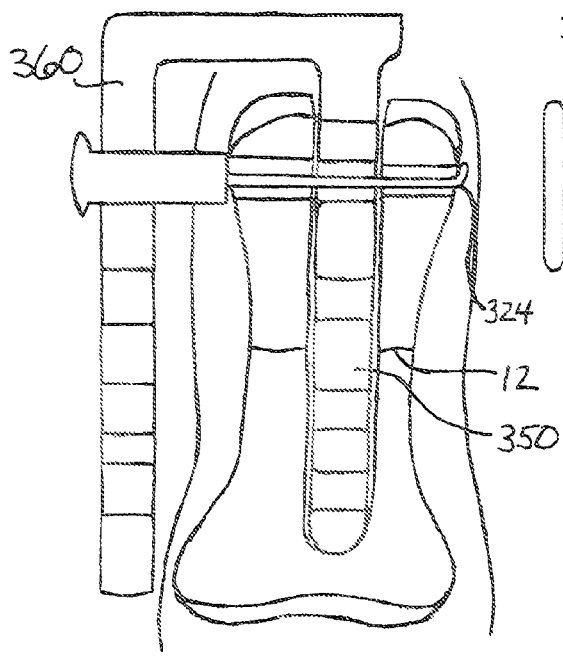
Figure 3F:
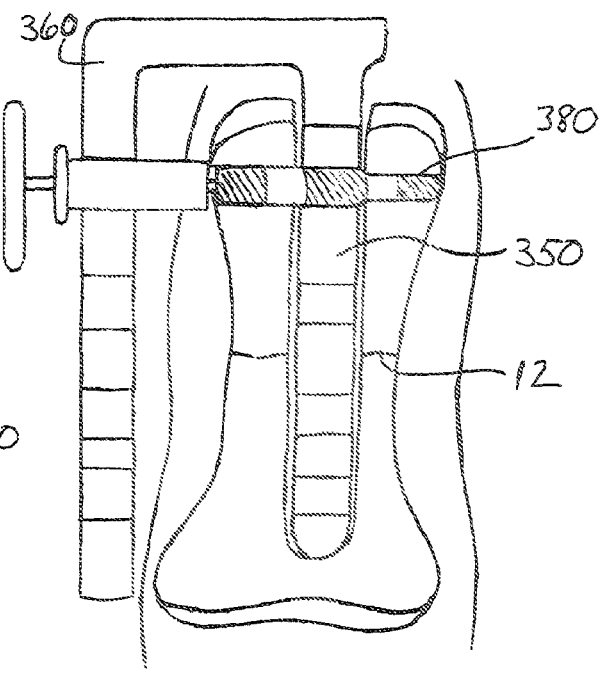
Figure 3G:
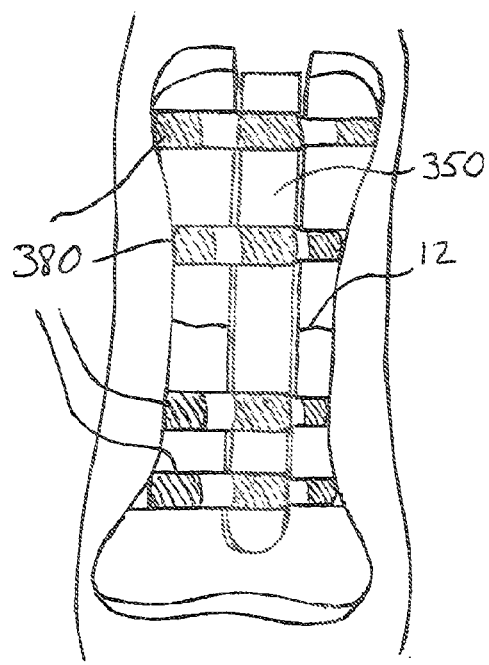
Figure 3H:
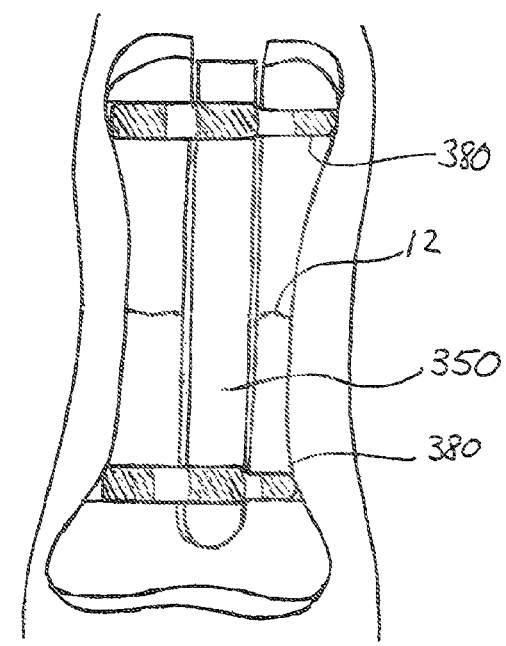

As shown in FIGS. 3A-3H, an alternative technique for introduction of the rods for the proximal and middle phalanges would be retrograde through the intercondylar notch of the head of the proximal or middle phalanges. For placement of the rod into the proximal phalanx for proximal phalanx fractures, an incision would be made at the proximal interphalangeal joint region dorsally and a small incision would be made through the extensor tendon. The proximal interphalangeal (PIP) joint would be flexed and the intercondylar notch of the PIP joint would be visualized between the two condyles of the proximal phalanx. As shown in FIGS. 3A and 3B, an opening 316 in the intercondylar notch 318 would be made with a small awl or drill 319 to allow access to the intramedullary canal 14 of the proximal phalanx. The articular cartilage 322 of the condyles, the main joint surface of the proximal interphalangeal joint, would be spared and remain intact. Then a guide wire 330 would be placed down the canal 14 across the fracture 12. As shown in FIG. 3B, reaming would be performed with one or a series of reamers 340 placed over the guide wire 330 to increase the size of the intramedullary canal. Then as shown in FIG. 3C, a rod 350 would be placed with an alignment jig 360 and hammer into the intramedullary canal. This technique would simplify the introduction of the intramedullary rod through a straight access to the intramedullary canal. The correct alignment of the fracture and position of the rod would be verified with fluoroscopic x ray. Rod 350 has holes 352a-352d, and jig 360 has guide holes 362a-362d, similarly aligned as in rod 50 and jig 60 in FIG. 4. With the alignment jig in place to line up with the cross locking holes of the rod, a small incision is made in the skin and dissection down to the bone is made. As shown in FIGS. 3D-3F, a soft tissue sleeve 370 is placed through the alignment jig until it is flush with the bone. A drill with drill bit 318 is used to drill across the medial and lateral cortices of the bone, and a measuring guide 324 is used to measure correct length. Then a headless cross locking screw 380 is placed through both cortices and through the hole in the rod, locking the rod in place. The screw is placed flush with the cortices so the extensor tendon can glide smoothly and not adhere to a prominent screw. The process is repeated for additional screws, and the alignment jig is then removed from the rod as shown in FIG. 3G. Correct alignment of the fracture 12 and hardware (rod 350 and screws 380) is verified by gross inspection and fluoroscopic x ray. The small incisions would be closed with suture. In various embodiments, similarly as described above with respect to FIGS. 2F-2H, two to four cross locking screws may be placed in rod 350. As shown in FIG. 3H, e.g., a single screw may be inserted at each of the proximal and distal ends of rod 350. In further embodiments, one or more additional screws may be inserted at either end of rod 350 as may be desired. Alignment jig 360 may include more than four guide holes and rod 350 may include more than four corresponding aligned holes therein to allow for selected spacing of cross screws 380. The holes in rod 350 and the guide holes in the alignment jig 360 may further be aligned at various angles to provide angled placement of screws through the bone fragments if desired. In further alternative embodiments, pegs 84 as shown in FIG. 7 having a threadless surface may instead be placed through holes in the rod 350 and bone to lock the rod in place by a friction fit between the pegs with the rod, or with the rod and the bone cortex.

In another embodiment of the invention, the rod may have transverse holes for the placement of proximal and distal locking screws, but also has angled holes in the center of the rod to place screws through the rod and have interfragmentary compression on an oblique fracture.

The base of the metacarpals, proximal and middle phalanges are angled. If introduction of the rod would be antegrade through the base of the bone, accommodation for the boney architecture may be made in the rod. For example the rod could be shaped with an appropriate angle or curve, as illustrated in FIGS. 2A-2H, to facilitate passage through the opening 16 and into canal 14. In another embodiment, the rod could be segmented such that it was flexible when the segmented pieces were loosely joined upon their insertion, and then made rigid by tightening the segmented pieces together after their insertion. One such form of flexible and tightenable segmented rod useful in the present invention is disclosed, e.g., in Chou et al. US 2008/0294163, the disclosure of which is incorporated by reference herein. In such a segmented rod embodiment, segments containing a hole for engagement with a locking screw or peg may be employed with the further segments described in Chou et al. While expanding petal segments described in Chou et al., which are designed for engagement with the internal wall of the canal, would not be necessary when employing locking screws or pegs in accordance with the present invention, they may additionally be employed if desired. If removal of the rod is necessary in the future, then the segmented pieces could be untightened to make the rod flexible again for ease of removal.

Another embodiment of the invention would be for the rod to be made of a metal that is relatively flexible at room temperature, but that when it is inserted into the bone hardens at body temperature. If the implant needs to be removed at a later date, then the finger could be cooled and the rod become flexible for removal. Ni—Ti alloys with a nickel content comprised between 40 and 52 atomic % pertain to the category of thermoelastic materials (also known in the field as Nitinol, Shape Memory Alloys, "smart" materials, etc.) may be employed in such an embodiment. Details of suitable processes and characteristics of these alloys may be found, for example, in C. M. Wayman, "Shape Memory Alloys" MRS Bulletin, April 1993, 49-56, M. Nishida et al., "Precipitation Processes in Near-Equiatimic TiNi Shape Memory Alloys", Metallurgical Transactions A, Vol 17A, September, 1986, 1505-1515, and H. Hosoda et al., "Martensitic transformation temperatures and mechanical properties of ternary NiTi alloys with off stoichiometric compositions", Intermetallics, 6(1998), 291-301, all of which are herein incorporated by reference in their entirety. Independently from the final shape of the Ni—Ti thermoelastic device, which can, for example, be wire-, tube-, sheet- or bar-based, the manufacturing process includes a cutting phase from a longer metallic piece, obtained from a semi-finished product resulting from an alloy melting process as described, for example, in U.S. Pat. No. 8,152,941, incorporated herein by reference in its entirety. The most common forms for the semi-finished products are long tubes, wires, rods, bars, sheets. The alloy can exist in either of two phases at room temperature, depending on the exact ratio of nickel to titanium atoms. Such materials exhibit a property such that atoms in the solid undergo a phase change wherein they are capable of subtly shifting their positions in response to a stimulus such as a change in temperature. The structure found above the temperature of the phase change possesses the high symmetry of a cube and is called austenite; the structure found below the temperature of the phase change is much less symmetric and is called martensite. In the martensite phase the material is relatively elastic, while in the austenite phase the material is comparatively rigid. Nitinol can be shaped while in the austenite phase by deforming it into the desired shape, e.g., a shape corresponding to the intramedullary canal. As it then cools below the phase transition temperature, the material enters the martensite phase. In the martensite phase the shape can then be changed by mechanical stress, as allowed by the less symmetric martensite structure. The sample will revert to the shape enforced upon it while it was in the austenite phase by returning it to the relatively rigid austenite phase through an increase in its temperature, such as being heated up to body temperature. The thermal energy acquired by the shape through heating it as its temperature is raised above the temperature corresponding to the phase change provides the energy the atoms need to return to their original positions and the sample to its original shape. This temperature may be tuned to be between room temperature and body temperature by varying the ratio of nickel to titanium atoms in the solid.

The rods and screws would be made of biocompatible materials, such as a titanium alloy composition with a combination of titanium, nickel, chromium, etc. In addition the rods would be shaped so that they fit appropriately into the intramedullary canal of each bone. A kit for intramedullary fixation of fractures of bones of the hand in accordance with an embodiment of the invention may include a series of rods with different size increments and lengths (e.g., a series of rods selected from lengths of from about 2 to 20 cm, in e.g., 0.2 cm increments) to match the corresponding bones (e.g., metacarpal, proximal, middle and distal phalanx) of the hand. The invention in a particular embodiment is advantageous with regard to fixation of fractures of the proximal and middle phalanx bones of the hand, wherein a series of rods selected from lengths of from about 2 to 10 cm are employed. There may also be differently shaped rods to match the corresponding bones of the right and left hands. Cross screws sized for such bones of the hand may have lengths of, e.g., from about 5 to 20 mm, more typically from about 10 to 15 mm, in e.g., 1 mm increments.

The invention advantageously enables immediate stability to a fracture with limited soft tissue injury or fracture disruption. This will facilitate fracture healing and faster functional recovery with less soft tissue and tendon complications. Fractures that could be treated with this implant are fractures of the shaft of the metacarpal, proximal phalanges or middle phalanges. The invention is also indicated for hand fractures that are comminuted, open fractures and fractures that have bone loss. This invention with the feature of locking screws provides the rotational and axial control necessary for maximum stability of the fractures that other rods have not provided. This will provide a stable fracture fixation for early motion allowing faster functional recovery.

While the invention is particularly useful with and has been described primarily with regard to treatment of fractures of bones of the hand, the use of an intramedullary rod fixation system employing headless cross locking screws or pegs in accordance with the invention will also be useful for other bones where the presence of locking screws or pegs projecting from the external surface of the bone may be problematic. In particular, the invention may be useful for fixing fractures in other long bones at positions having little soft tissue or muscle coverage between the bone and the skin, such as at the distal tibia (i.e., near the ankle joint), and proximal tibia and distal femur (i.e., near the knee joint) locations.

While the invention has been described in connection with several presently preferred embodiments thereof, those skilled in the art will appreciate that many modifications and changes may be made without departing from the true spirit and scope of the invention which accordingly is intended to be defined solely by the appended claims.

The invention claimed is:

1. A method for fixation of a fracture of a bone of the hand having an intramedullary canal comprising:
    inserting an intramedullary rod into the intramedullary canal of the bone of the hand, wherein the intramedullary rod includes at least one proximal hole and at least one distal hole;
    inserting a proximal screw or peg through the bone and through the at least one proximal hole; and
    inserting a distal screw or peg through the bone and through the at least one distal hole;
    wherein each of the proximal and the distal screws or pegs are headless screws or pegs and are selected to have a size and are inserted through the proximal and distal holes in the rod such that the screws or pegs do not extend substantially beyond an exterior surface of the bone and are flush with the medial and lateral cortex of the bone.

2. The method of claim 1, wherein each of the proximal and distal screws or pegs is locked in place by a friction fit with, or screw threads in, the proximal and distal holes of the intramedullary rod.

3. The method of claim 1, wherein each of the proximal and distal screws or pegs is a screw locked in place by screw threads in the proximal and distal holes of the intramedullary rod.

4. The method of claim 1, wherein each of the proximal and distal screws or pegs is a screw locked in place by threads of the screw engaging the bone.

5. The method of claim 1, wherein each of the proximal and distal screws or pegs is a screw locked in place by threads of the screw engaging the bone and by screw threads in the proximal and distal holes of the intramedullary rod.

6. The method of claim 5, wherein the threads of the screw engaging the bone and screw threads in the hole of the intramedullary rod are of the same screw thread pitch.

7. The method of claim 5, wherein the screw comprises distinct portions having different diameters along the length of the screw so as to provide a tapered diameter along the length of the screw, the screw diameter being narrower at an end portion at the far cortex end than the diameter of the screw in a central portion where the screw engages the screw threads in the hole of the intramedullary rod.

8. The method of claim 7, wherein the screw diameter at a headless end portion of the screw at the near cortex end is greater than or equal to the diameter of the screw in the central portion where the screw engages the screw threads in the hole of the intramedullary rod.

9. The method of claim 1, wherein the bone is a metacarpal or phalangeal bone of the hand.

10. The method of claim 9, wherein the intramedullary rod is percutaneously inserted into the intramedullary canal of the bone.

11. The method of claim 10, wherein the at least one proximal screw or peg and the at least one distal screw or peg are percutaneously inserting through the bone and through the at least one proximal hole and the at least one distal hole, respectively.

12. The method of claim 11, wherein the at least one proximal locking screw or peg is aligned with the proximal hole through a first guide hole in an alignment jig releasably attached to the intramedullary rod, and the at least one distal locking screw or peg is aligned with the distal hole through a second guide hole in the alignment jig.

13. The method of claim 1, wherein the at least one proximal locking screw or peg is aligned with the proximal hole through a first guide hole in an alignment jig releasably attached to the intramedullary rod, and the at least one distal locking screw or peg is aligned with the distal hole through a second guide hole in the alignment jig.

14. The method of claim 1, wherein the bone is a metacarpal or phalangeal bone of the hand, wherein the intramedullary rod is percutaneously inserted antegrade into the intramedullary canal of the bone, and wherein the intramedullary rod is shaped with a curve to facilitate passage through an opening made in the base of the bone and into the canal.

* * * * *